(12) United States Patent
Przybyszewski

(10) Patent No.: US 7,912,552 B2
(45) Date of Patent: Mar. 22, 2011

(54) MEDICAL ELECTRICAL DEVICE INCLUDING NOVEL MEANS FOR REDUCING HIGH FREQUENCY ELECTROMAGNETIC FIELD-INDUCED TISSUE HEATING

(75) Inventor: Piotr Przybyszewski, Coon Rapids, MN (US)

(73) Assignee: Medtronic, Inc., Minneapolis, MN (US)

( * ) Notice: Subject to any disclaimer, the term of this patent is extended or adjusted under 35 U.S.C. 154(b) by 136 days.

(21) Appl. No.: 10/889,523

(22) Filed: Jul. 12, 2004

(65) Prior Publication Data

US 2006/0009819 A1    Jan. 12, 2006

(51) Int. Cl.
*A61N 1/00* (2006.01)
(52) U.S. Cl. ......................................................... 607/72
(58) Field of Classification Search .................... 607/72, 607/116, 36, 63, 4, 5, 122, 27
See application file for complete search history.

(56) References Cited

U.S. PATENT DOCUMENTS

| | | | |
|---|---|---|---|
| 3,243,738 A | 3/1966 | Schlicke et al. | |
| 5,217,010 A | 6/1993 | Tsitlik et al. | 128/419 PG |
| 5,243,911 A * | 9/1993 | Dow et al. | 102/202.2 |
| 6,437,664 B1 | 8/2002 | Meppelink et al. | |
| 6,553,910 B2 * | 4/2003 | Fogle, Jr. | 102/202.2 |
| 6,589,237 B2 * | 7/2003 | Woloszko et al. | 606/41 |
| 6,985,347 B2 * | 1/2006 | Stevenson et al. | 361/302 |
| 6,999,818 B2 * | 2/2006 | Stevenson et al. | 607/37 |
| 7,013,180 B2 * | 3/2006 | Dougherty et al. | 607/116 |
| 7,038,900 B2 * | 5/2006 | Stevenson et al. | 361/302 |
| 2003/0050557 A1 * | 3/2003 | Susil et al. | 600/424 |
| 2003/0083723 A1 | 5/2003 | Wilkinson et al. | 607/122 |
| 2003/0083726 A1 * | 5/2003 | Zeijlemaker et al. | 607/122 |
| 2003/0097126 A1 * | 5/2003 | Woloszko et al. | 606/41 |
| 2003/0125773 A1 * | 7/2003 | Havel et al. | 607/7 |
| 2003/0144716 A1 | 7/2003 | Reinke et al. | 607/116 |
| 2003/0144721 A1 * | 7/2003 | Villaseca et al. | 607/122 |
| 2004/0088012 A1 * | 5/2004 | Kroll et al. | 607/9 |
| 2005/0197677 A1 * | 9/2005 | Stevenson | 607/36 |
| 2005/0240100 A1 * | 10/2005 | Wang et al. | 600/431 |

FOREIGN PATENT DOCUMENTS

| | | |
|---|---|---|
| WO | WO02083236 A | 10/2002 |
| WO | WO03063946 A | 8/2003 |

* cited by examiner

*Primary Examiner* — George Manuel
*Assistant Examiner* — Robert N Wieland
(74) *Attorney, Agent, or Firm* — Carol F. Barry

(57) ABSTRACT

A medical device including an elongate lead connected to a pulse generator connector further includes a passive lossy circuit electrically connected in between a distal portion of the lead conductor and the high frequency-grounded surface. The passive lossy circuit has a high frequency impedance approximately equal to a characteristic impedance of the lead when implanted in a body and dissipates energy of an incident wave formed along the lead, thereby diminishing a reflection of the incident wave, the incident wave being induced by exposure of the medical device to a high frequency electromagnetic field. The passive lossy circuit further has low pass properties allowing for normal device operation.

51 Claims, 4 Drawing Sheets

US 7,912,552 B2

MEDICAL ELECTRICAL DEVICE INCLUDING NOVEL MEANS FOR REDUCING HIGH FREQUENCY ELECTROMAGNETIC FIELD-INDUCED TISSUE HEATING

TECHNICAL FIELD

Embodiments of the present invention relate generally to a medical device including electrical leads and more particularly to means incorporated within the device for reducing high frequency electromagnetic field-induced tissue heating in the vicinity of a lead electrode.

BACKGROUND

The technology explosion in the implantable medical devices industry has resulted in many new and innovative devices and methods for analyzing and improving the health of a patient. The class of implantable medical devices now includes pacemakers, cardioverters, defibrillators, neural stimulators, and drug administering devices, among others. Often these devices are operatively coupled with electrodes, many of which are mounted on elongate lead bodies carrying conductors, which couple the electrodes to the devices.

Patients, in which such leads are implanted, may be exposed to a substantial amount of radio frequency (RF) energy, for example when subject to MRI scans or radio diathermy processes. The lead generally acts as an antenna during exposure to radio frequency signals, thus, in the presence of these signals, an appreciable amount of current may be generated in a lead resulting in a high current concentration at a surface of a tissue-contacting electrode. Much of this current, which is converted to heat, due to the energy loss caused by a resistance of the electrode-to-tissue interface, may result in tissue damage in proximity to the electrode.

BRIEF DESCRIPTION OF THE DRAWINGS

The following drawings are illustrative of particular embodiments of the invention and therefore do not limit its scope, but are presented to assist in providing a proper understanding of the invention. The drawings are not to scale (unless so stated) and are intended for use in conjunction with the explanations in the following detailed description. The present invention will hereinafter be described in conjunction with the appended drawings, wherein like numerals denote like elements, and.

DETAILED DESCRIPTION

The following detailed description is exemplary in nature and is not intended to limit the scope, applicability, or configuration of the invention in any way. Rather, the following description provides a practical illustration for implementing exemplary embodiments of the invention.

Figure 1:
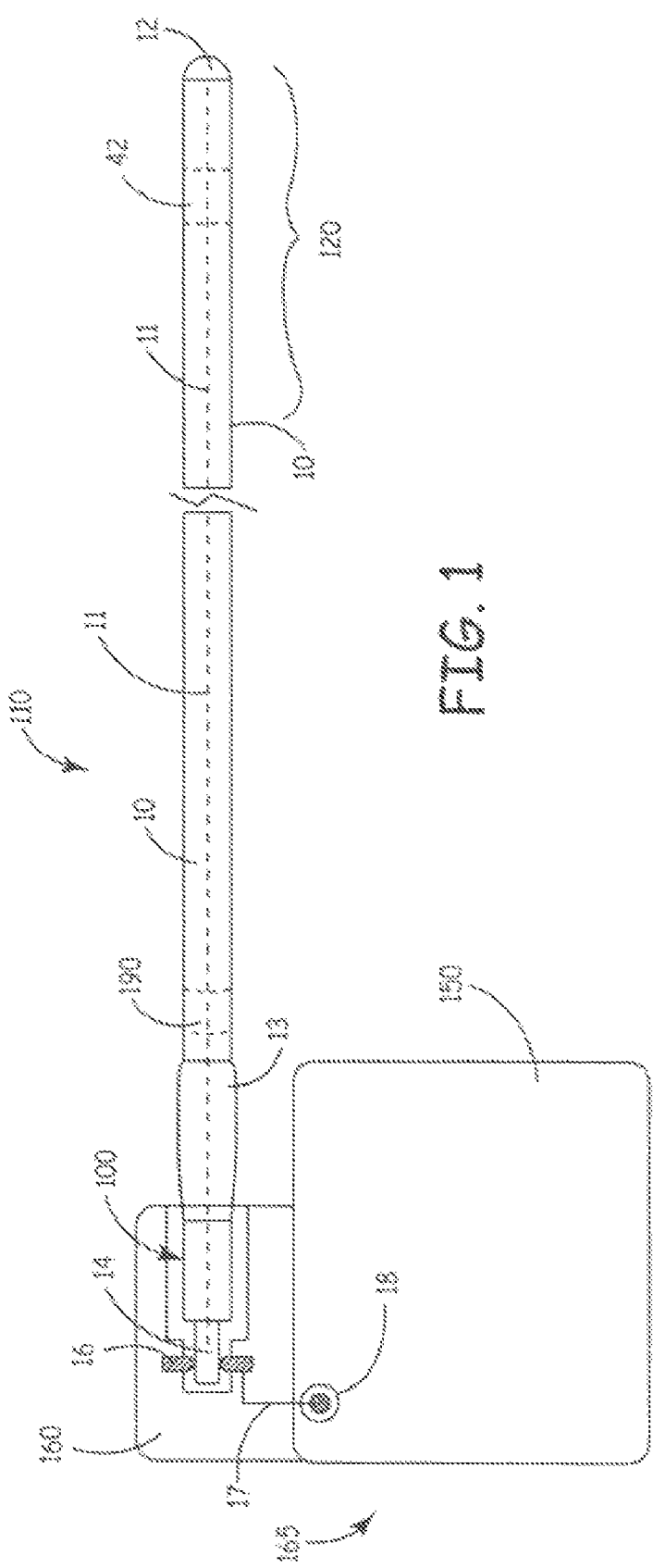
FIG. 1 is a plan view of an exemplary medical device in which embodiments of the present invention may be incorporated.

FIG. 1 is a plan view of an exemplary medical electrical device in which embodiments of the present invention may be incorporated. FIG. 1 illustrates a pulse generator 165 including a hermetically sealed enclosure or housing 150, which contains a battery and electronic circuitry (not shown), and a connector module 160 fixedly attached to housing 150; an elongate lead 110 is connected to pulse generator 165 within a bore of connector module 160 where a conductive contact 16 makes electrical contact with a connector element 14 that terminates a proximal portion or connector 100 of lead 110. According to the illustrated embodiment a signal conductor 17, which is electrically connected to the electronic circuitry contained within housing 150, extends out through a feedthrough 18 of housing 150 and into connector module 160 where it connects to contact 16. FIG. 1 further illustrates lead 110 including an elongate insulative body 10, which is joined to connector 100 by a connector sleeve 13, extends distally from connector 100, and carries an elongate conductor 11; elongate conductor 11 connects connector element 14 to an electrode 12, terminating a distal portion 120 of lead body 10, in order to operatively couple electrode 12 with pulse generator 165.

Figure 2:
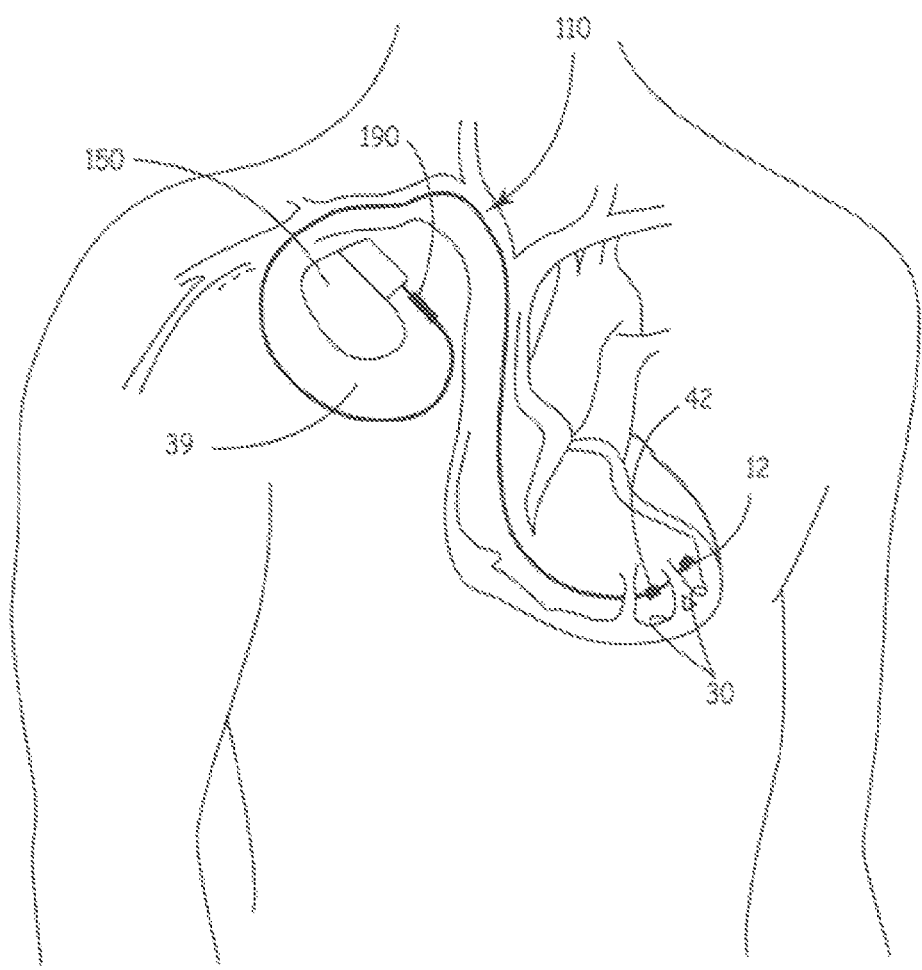
FIG. 2 is a schematic showing the device of FIG. 1 implanted in a patient.

According to embodiments of the present invention a passive lossy circuit, examples of which will be described in conjunction with FIGS. 3A-D, is incorporated into the device, such that the passive lossy circuit is electrically connected to conductor 11 and to a high frequency grounded surface, for example housing 150 or an exterior conductive surface 190 of lead 110, which may be a ring connected to conductor 11 and formed about lead body 10, as shown by dashed lines. When the device is implanted in a body, for example as illustrated in FIG. 2, the high frequency grounded surface is in contact with subcutaneous tissue within a pectoral pocket 39 and electrode 12 contacts endocardial tissue in proximity to a zone 30. In order to dissipate energy of an incident wave traveling along lead 110 toward pulse generator 165, the incident wave having been induced by exposure of the implanted device to a high frequency electromagnetic field, and thereby diminish a reflection of the incident wave being reflected distally to electrode 12, the passive lossy circuit has a high frequency impedance approximately equal to a characteristic impedance of the implanted lead 110. It should be noted that passive lossy circuits according to the present invention have low pass properties allowing for normal device operation.

Figure 3A:
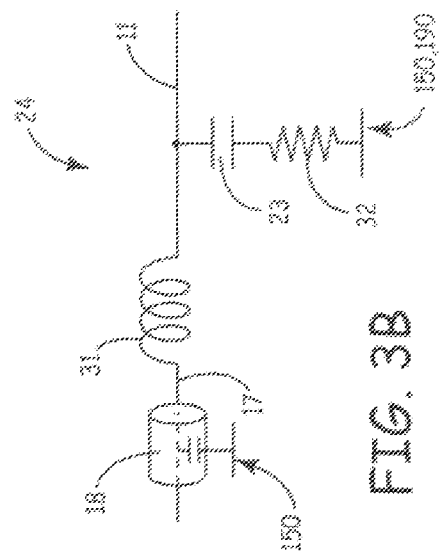
FIGS. 3A-C are circuit diagrams according to alternate embodiments of the present invention.
Figure 3B:
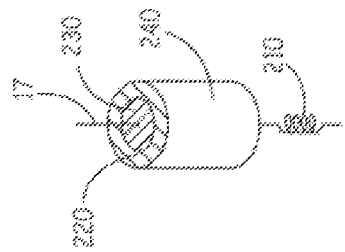

FIGS. 3A-B are circuit diagrams of alternate embodiments of passive lossy circuits. According to the exemplary embodiments depicted in FIGS. 3A-D, the high frequency grounded surface has a high frequency impedance less than the characteristic impedance of lead 110, preferably equal to or greater than an order of magnitude less, resistors have a resistance approximating the characteristic impedance, inductors have an impedance higher than the characteristic impedance, preferably equal to or greater than an order of magnitude higher, at the high frequencies, and capacitors act as a "short", or have a relatively low impedance, at the high frequencies.

Radio frequency (RF) signal coupled current present around the lead may cause a current flow in the lead. In the presence of significant electromagnetic fields, such as fields present during MRI processes, a substantial amount of RF signal-coupled energy may be present. The electrical energy generally occurs at the high RF frequencies, such as the MRI frequencies of 64 MHz and/or 128 MHz, or such as a radio diathermy frequency 27 MHz.

FIG. 3A illustrates a passive lossy circuit 20 formed by an inductor 21 in parallel with a resistor 22 and electrically connected to conductor 11 and signal wire 17; referring back to FIG. 1, circuit 20 may be physically incorporated into connector module 160, in proximity to contact 16, into lead connector 100, in proximity to connector element 14, or into lead body in proximity to connector sleeve 13. FIG. 3A further illustrates feedthrough 18 as a capacitive element between signal wire and housing 150, which, in this case is the high frequency grounded surface. FIG. 3B illustrates a passive lossy circuit 24 formed by a capacitor 23 in series with a resistor 32, both in parallel with an inductor 31, and electrically connected to conductor 11 and signal wire 17.

FIG. 3B further illustrates feedthrough 18 as a capacitive element between signal wire 17 and housing 150, which according to one embodiment exclusively forms the high frequency grounded surface, while, according to another embodiment, forms the high frequency grounded surface along with surface 190 of lead 110. According to the former embodiment, the entirety of circuit 24 would be physically incorporated into connector module 160, while, according to the latter embodiment, circuit 24 need not be incorporated into connector module 160 but could be incorporated into lead body in proximity to surface 190.

Figure 3C:
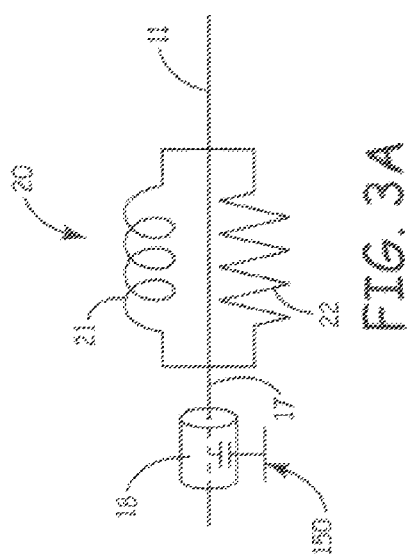
Figure 3D:
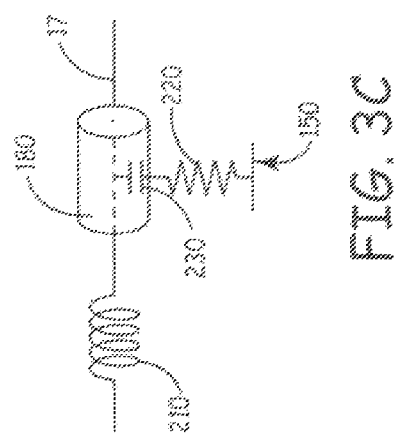
FIG. 3D is a perspective detail view of a feedthrough according to the embodiment illustrated in FIG. 3C.

FIG. 3C is a circuit diagram of yet another embodiment of the present invention and FIG. 3D is a perspective detail view of a feedthrough according to the embodiment illustrated in FIG. 3C. FIG. 3C illustrates a passive lossy circuit including a capacitor 230 in series with a resistor 220 both in parallel with an inductor 210; capacitor 230 and resistor 220 are incorporated in conjunction with a feedthrough 180, being coupled to the high frequency grounded surface formed by housing 150, and inductor 210 is electrically connected between the electronic circuitry, contained within housing 150, and signal wire 17. FIG. 3D illustrates feedthrough 180 including capacitor 230 as an inner layer and resistor 220 as an outer layer of an insulator 240 formed about signal wire 17; according to an alternate embodiment the positions of insulator layers are switched so that capacitor 230 is an outer layer and resistor 220 is an inner layer.

Figure 4A:
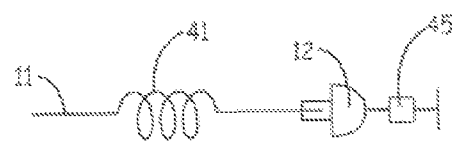
FIG. 4A-C are schematic diagrams according to further embodiments of the present invention.
Figure 4B:
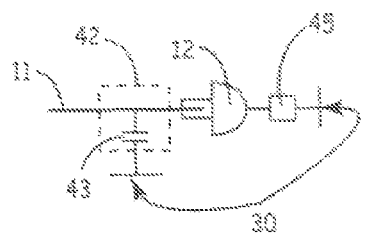
Figure 4C:
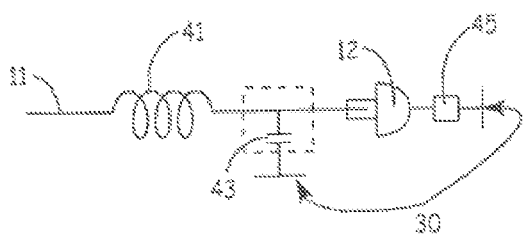

FIGS. 4A-C are schematic diagrams according to further embodiments of the present invention. FIGS. 4A-C illustrate alternative passive non-lossy circuits, each of which could be incorporated into the system illustrated in FIG. 1 in conjunction with a passive lossy circuit, for example one of those described in conjunction with FIGS. 3A-D; a non-lossy circuit would be positioned within distal portion 120 of lead 110 in proximity to electrode 12. According to the embodiments of the present invention exemplified in FIGS. 4A-C, the passive non-lossy circuit has a high frequency impedance such that a combined impedance of the non-lossy circuit and an electrode-to-tissue interface impedance 45 is different from, either higher or lower than, the characteristic impedance of lead 110; the difference between the combined impedance and the characteristic impedance is preferably equal to or greater than an order of magnitude. Thus, the passive non-lossy circuit enhances a reflection of an incident wave traveling along lead 110 toward electrode 12, the incident wave having been induced by a high frequency electromagnetic field, and thereby diminishes current flow to electrode 12. The passive lossy circuit, for example any of the embodiments described in conjunction with FIGS. 3A-D, by dissipating power to diminish reflection of incident waves traveling toward pulse generator 165, assists the passive non-lossy circuit in reducing power dissipated in the tissue in the vicinity of electrode 12, i.e. in zone 30 (FIG. 2).

FIG. 4A illustrates a passive non-lossy circuit including an inductor 41 in series with conductor 11 and electrode 12; US patent application 2003/0144721 further describes embodiments of FIG. 4A and is incorporated herein, by reference, in its entirety. FIG. 4B illustrates an alternative passive non-lossy circuit including a capacitor 43 in parallel with electrode 12 and grounded by means of conductive surface 42 (FIG. 1) in proximity to tissue at a zone 30 (FIG. 2). FIG. 4C illustrates yet another embodiment wherein a combination of inductor 41 and capacitor 43 are grounded by surface 42. It should be noted that passive non-lossy circuits according to embodiments of the present invention have low pass properties allowing for normal device operation.

In the forgoing detailed description, the invention has been described with reference to specific embodiments. However, it may be appreciated that various modifications and changes can be made without departing from the scope of the invention as set forth in the appended claims.

What is claimed is:

1. A medical device, comprising:
   an electrical lead including an elongate insulative body, an elongate lead conductor extending within the insulative body between a proximal end and a distal end, a connector element electrically connected to the lead conductor and terminating the proximal end of the lead conductor;
   a housing containing electronic circuitry and including a feedthrough; the feedthrough including a signal conductor electrically connected to the electronic circuitry and extending out from the housing through the feedthrough;
   a connector module attached to the housing and including a conductive contact electrically connected to the signal conductor and adapted to electrically connect to the connector element of the lead at the proximal end of the lead conductor;
   a high frequency-grounded surface; and
   a passive lossy circuit electrically connected in proximity to and closer to the proximal end of the lead conductor than the distal end and in between the lead conductor and the high frequency-grounded surface when the conductive contact is connected to the connector element;
   wherein the passive lossy circuit located in proximity to the proximal end of the lead conductor has a high frequency impedance approximately equal to a characteristic impedance of the lead when implanted in a body such that the passive lossy circuit dissipates energy of an incident wave induced when the medical device is exposed to a high frequency electromagnetic field at high frequencies comprising at least one of 27 MHz, 64 MHz, and 128 MHz, formed along the lead, and traveling toward the proximal end of the lead conductor, thereby diminishing reflection of the incident wave toward the distal end; and
   the passive lossy circuit has low pass properties allowing for normal device operation when the conductive contact of the connector module is electrically connected to the connector element of the lead.

2. The device of claim 1, wherein the high frequency-grounded surface has a high frequency impedance less than the characteristic impedance of the lead.

3. The device of claim 1, wherein the high frequency-grounded surface comprises an outer surface of the housing.

4. The device of claim 1, wherein the high frequency-grounded surface comprises an outer surface on the insulative body.

5. The device of claim 1, wherein the passive lossy circuit is positioned along the lead conductor in proximity to the connector element.

6. The device of claim 1, wherein the passive lossy circuit is positioned within the connector module.

7. The device of claim 1, wherein the passive lossy circuit is positioned in the housing, the passive lossy circuit being formed in part by the feedthrough.

8. The device of claim 1, wherein the high frequency-grounded surface has a high frequency impedance of at least one order of magnitude less than the characteristic impedance of the lead.

9. The device of claim 1, further comprising:
a lead connector on which the connector element is mounted; and
a connector sleeve extending from the lead connector to the insulative body of the lead;
wherein the passive lossy circuit is positioned in proximity to the connector sleeve.

10. The device of claim 1, further comprising:
a lead connector on which the connector element is mounted; and
a connector sleeve extending from the lead connector to the insulative body of the lead;
wherein the passive lossy circuit is positioned within the lead connector.

11. The device of claim 1, wherein the passive lossy circuit comprises a parallel resistor and inductor, wherein the resistor has a resistance approximately equal to the characteristic impedance of the lead.

12. The device of claim 1, wherein the passive lossy circuit comprises a series resistor and capacitor in parallel with an inductor, wherein the resistor has a resistance approximately equal to the characteristic impedance of the lead.

13. The device of claim 12, wherein:
the feedthrough includes an insulator surrounding the signal conductor, the insulator including a first part and a second part surrounding the first part; and
the capacitor is formed by the first part of the insulator and the resistor is formed by the second part of the insulator.

14. The device of claim 12, wherein:
the feedthrough includes an insulator surrounding the signal conductor, the insulator including a first part and a second part surrounding the first part; and
the resistor is formed by the first part of the insulator and the capacitor is formed by the second part of the insulator.

15. The device of claim 1, wherein:
the electrical lead further includes an electrode connected to and terminating the distal end of the lead conductor; and further wherein a passive non-lossy circuit is electrically connected between the lead conductor and the electrode and positioned in proximity to the electrode closer to the distal end of the lead conductor than the proximal end of the lead conductor;
the passive non-lossy circuit has a high frequency impedance such that a combined impedance of the non-lossy circuit and an electrode-to-tissue interface impedance, when the lead is implanted in the body, is different from the characteristic impedance of the lead to enhance a reflection of an incident wave traveling toward the electrode and thereby minimize energy of the incident wave traveling toward the electrode being dissipated at the electrode-to-tissue interface; the incident wave traveling toward the electrode being induced by exposure of the medical device to the high frequency electromagnetic field; and
the passive non-lossy circuit has low pass properties allowing for normal device operation when the conductive contact of the connector module is electrically connected to the connector element of the lead.

16. The device of claim 15, wherein the passive non-lossy circuit comprises an inductor in series with the electrode.

17. The device of claim 15, wherein the passive non-lossy circuit comprises a capacitor in parallel with the electrode and further connected to a conductive surface in contact with a portion of tissue.

18. The device of claim 16, wherein the passive non-lossy circuit further comprises a capacitor in parallel with the electrode and further connected to a conductive surface in contact with a portion of tissue.

19. The device of claim 15, wherein the electrode comprises a tip electrode terminating the distal end of the lead conductor.

20. The device of claim 19, wherein the passive non-lossy circuit comprises a capacitor in parallel with the electrode and further comprising a conductive surface formed about the insulative body in contact with a portion of tissue.

21. The device of claim 20, wherein the passive non-lossy circuit further comprises an inductor in series with the electrode.

22. A medical electrical lead comprising:
an elongate insulative body;
an elongate lead conductor extending within the body between a proximal end and a distal end;
a connector element electrically connected to the lead conductor and terminating the proximal end of the lead conductor, the connector element at the proximal end of the lead conductor being adapted to electrically connect with a pulse generator for forming a medical device; and
a passive lossy circuit electrically connected in proximity to and closer to the proximal end of the lead conductor than the distal end;
wherein the passive lossy circuit connected in proximity to the proximal end has a high frequency impedance approximately equal to a characteristic impedance of the lead when implanted in a body such that the passive lossy circuit dissipates energy of an incident wave induced when the medical device is exposed to a high frequency electromagnetic field at high frequencies comprising at least one of 27 MHz, 64 MHz, and 128 MHz, formed along the lead, and traveling toward the proximal end of the lead conductor, thereby diminishing reflection of the incident wave toward the distal end; and
the passive lossy circuit has low pass properties allowing for normal device operation when the lead is electrically connected to the pulse generator.

23. The lead of claim 22, further comprising a high frequency-grounded surface electrically connected to the lead conductor, the surface being connected in between the passive lossy circuit and the connector element.

24. The lead of claim 23, wherein the high frequency-grounded surface has a high frequency impedance less than the characteristic impedance of the lead.

25. The lead of claim 22, wherein the passive lossy circuit is positioned along the lead conductor in proximity to the connector element.

26. The lead of claim 22, further comprising:
a lead connector on which the connector element is mounted; and
a connector sleeve extending from the lead connector to the insulative body;
wherein the passive lossy circuit is positioned in proximity to the connector sleeve.

27. The lead of claim 22, further comprising:
a lead connector on which the connector element is mounted; and
a connector sleeve extending from the lead connector to the insulative body;

wherein the passive lossy circuit is positioned within the lead connector.

28. The lead of claim 22, wherein the passive lossy circuit comprises a parallel resistor and inductor, wherein the resistor has a resistance approximately equal to the characteristic impedance of the lead.

29. The lead of claim 22, wherein the passive lossy circuit comprises a series resistor and capacitor in parallel with an inductor, wherein the resistor has a resistance approximately equal to the characteristic impedance of the lead.

30. The lead of claim 23, wherein the high frequency-grounded surface comprises an outer surface on the insulative body.

31. The lead of claim 23, wherein the high frequency-grounded surface has a high frequency impedance of at least one order of magnitude less than the characteristic impedance of the lead.

32. The lead of claim 22, further comprising:
an electrode connected to and terminating the distal end of the lead conductor; and
a passive non-lossy circuit electrically connected between the passive lossy circuit and the electrode and positioned in proximity to the electrode closer to the distal end of the lead conductor than the proximal end of the lead conductor;
wherein the passive non-lossy circuit has a high frequency impedance such that a combined impedance of the passive non-lossy circuit and an electrode-to-tissue interface impedance, when the lead is implanted in the body, is different from the characteristic impedance of the lead to enhance a reflection of an incident wave traveling toward the electrode and thereby minimize energy of the incident wave traveling toward the electrode being dissipated at the electrode-to-tissue interface; the incident wave traveling toward the electrode being induced by exposure of the medical device to the high frequency electromagnetic field; and
the passive non-lossy circuit has low pass properties allowing for normal device operation when the lead is electrically connected to the pulse generator.

33. The lead of claim 32, wherein the passive non-lossy circuit comprises an inductor in series with the electrode.

34. The lead of claim 32, wherein the passive non-lossy circuit comprises a capacitor in parallel with the electrode and further connected to a conductive surface in contact with a portion of tissue.

35. The lead of claim 33, wherein the passive non-lossy circuit further comprises a capacitor in parallel with the electrode and further connected to a conductive surface in contact with a portion of tissue.

36. A medical pulse generator comprising:
a housing containing electronic circuitry and including a feedthrough; the feedthrough including a signal conductor electrically connected to the electronic circuitry and extending out from the housing through the feedthrough;
a connector module attached to the housing and including a conductive contact electrically connected to the signal conductor and adapted to electrically connect to a connector element of a medical lead to form a medical device;
a high frequency-grounded surface electrically connected in between the conductive contact and the electronic circuitry; and
a passive lossy circuit electrically connected in between the conductive contact and the high frequency-grounded surface;

wherein the passive lossy circuit has a high frequency impedance approximately equal to a characteristic impedance of the medical lead when the lead is electrically connected to the conductive contact and implanted in a body such that the passive lossy circuit dissipates energy of an incident wave induced when the medical device is exposed to a high frequency electromagnetic field at high frequencies comprising at least one of 27 MHz, 64 MHz, and 128 MHz, formed along the lead, and traveling toward the proximal end of the lead conductor, thereby diminishing reflection of the incident wave toward the distal end; and
the passive lossy circuit has low pass properties allowing for normal device operation when the conductive contact of the connector module is electrically connected to the lead.

37. The pulse generator of claim 36, wherein the high frequency-grounded surface has a high frequency impedance less than the characteristic impedance of the lead.

38. The pulse generator of claim 36, wherein the high frequency-grounded surface comprises an outer surface of the housing.

39. The pulse generator of claim 36, wherein the high frequency-grounded surface has a high frequency impedance of at least one order of magnitude less than the characteristic impedance of the lead.

40. The pulse generator of claim 36, wherein the passive lossy circuit is positioned within the connector module.

41. The pulse generator of claim 36, wherein the passive lossy circuit is positioned within the housing, the passive lossy circuit being formed in part by the feedthrough.

42. The pulse generator of claim 36, wherein the passive lossy circuit comprises a parallel resistor and inductor, wherein the resistor has a resistance approximately equal to the characteristic impedance of the lead.

43. The pulse generator of claim 36, wherein the passive lossy circuit comprises a series resistor and capacitor in parallel with an inductor, wherein the resistor has a resistance approximately equal to the characteristic impedance of the lead.

44. The pulse generator of claim 43, wherein:
the feedthrough includes an insulator surrounding the signal conductor, the insulator including a first part and a second part surrounding the first part; and
the capacitor is formed by the first part of the insulator and the resistor is formed by the second part of the insulator.

45. The pulse generator of claim 43, wherein:
the feedthrough includes an insulator surrounding the signal conductor, the insulator including a first part and a second part surrounding the first part; and
the resistor is formed by the first part of the insulator and the capacitor is formed by the second part of the insulator.

46. A medical device, comprising:
an electrical lead including an elongate insulative body, an elongate lead conductor extending within the body between a proximal end and a distal end, a connector element electrically connected to the lead conductor and terminating the proximal end of the lead conductor and an electrode connected to and terminating a distal end of the lead conductor;
a housing containing electronic circuitry and including a feedthrough; the feedthrough including a signal conductor electrically connected to the electronic circuitry and extending out from the housing through the feedthrough;

a connector module attached to the housing and including a conductive contact electrically connected to the signal conductor and adapted to electrically connect to the connector element of the lead;

a high frequency-grounded surface;

a passive lossy circuit electrically connected in proximity to and closer to the proximal end of the lead conductor than the distal end in between the lead conductor and the high frequency-grounded surface when the conductive contact is connected to the connector element; and a passive non-lossy circuit electrically connected between the conductor and the electrode and positioned in proximity to the electrode closer to the distal end of the lead conductor than the proximal end;

wherein the passive lossy circuit has a high frequency impedance approximately equal to a characteristic impedance of the lead when implanted in a body such that the passive lossy circuit dissipates energy of an incident wave induced when the medical device is exposed to a high frequency electromagnetic field at high frequencies comprising at least one of 27 MHz, 64 MHz, and 128 MHz, formed along the lead, and traveling toward the proximal end of the lead conductor, thereby diminishing reflection of the incident wave toward the distal end;

the passive lossy circuit has low pass properties allowing for normal device operation when the conductive contact of the connector module is electrically connected to the connector element of the lead;

the passive non-lossy circuit has a high frequency impedance such that a combined impedance of the non-lossy circuit and an electrode-to-tissue interface impedance, when the lead is implanted in the body, is different from the characteristic impedance of the lead to enhance a reflection of an incident wave traveling toward the electrode and thereby minimize energy of the incident wave traveling toward the electrode being dissipated at the electrode-to-tissue interface;

the passive non-lossy circuit has low pass properties allowing for normal device operation when the conductive contact of the connector module is electrically connected to the connector element of the lead.

47. A medical device comprising:
a housing;
a connector module coupled to the housing;
a lead, wherein the lead includes a proximal end coupled to the connector module and a distal end;
a high frequency-grounded surface disposed on at least one of the housing and the lead;
a passive lossy circuit directly coupled to the high frequency-grounded surface, the passive lossy circuit disposed at the proximal end of the lead; and
a reflective circuit, disposed closer to the distal end of the lead than the proximal end of the lead, comprises a high frequency impedance, at high frequencies comprising at least one of 27 MHz, 64 MHz, and 128 MHz, having an order of magnitude difference than the characteristic impedance of the lead,
wherein the passive lossy circuit has a high frequency impedance, at high frequencies comprising at least one of 27 MHz, 64 MHz, and 128 MHz, about equal to a characteristic impedance of the lead when implanted in a body.

48. A medical device comprising:
a housing;
a connector module coupled to the housing;
a lead, wherein the lead includes a proximal end coupled to the connector module and a distal end;
a high frequency-grounded surface disposed on at least one of the housing and the lead;
a passive lossy circuit directly coupled to the high frequency-grounded surface, the passive lossy circuit disposed at the proximal end of the lead, the passive lossy circuit includes a high frequency impedance about equal to a characteristic impedance of the lead when implanted in a body; and
a reflective circuit, disposed closer to the distal end of the lead than the proximal end of the lead, comprises a high frequency impedance having an order of magnitude difference than the characteristic impedance of the lead, wherein the reflective circuit comprises one or more reactive elements selected from a group comprising at least inductors and capacitors, wherein inductors of the reflective circuit that are present provide an impedance equal to or greater than an order of magnitude higher than the characteristic impedance at high frequencies comprising at least one of 27 MHz, 64 MHz, and 128 MHz, and capacitors of the reflective circuit that are present act as a short or have a relatively low impedance at high frequencies comprising at least one of 27 MHz, 64 MHz, and 128 MHz, and further wherein the one or more reactive elements provide the high frequency impedance having an order of magnitude difference than the characteristic impedance of the lead so as to provide for reflection of a high frequency wave induced by exposure of the lead to a high frequency electromagnetic field at high frequencies comprising at least one of 27 MHz, 64 MHz, and 128 MHz,
wherein the passive lossy circuit comprises at least one resistive element and one or more reactive elements selected from a group comprising at least inductors and capacitors, wherein inductors that are present provide an impedance equal to or greater than an order of magnitude higher than the characteristic impedance at high frequencies comprising at least one of 27 MHz, 64 MHz, and 128 MHz and capacitors that are present act as a short or have a relatively low impedance at high frequencies comprising at least one of 27 MHz, 64 MHz, and 128 MHz, and further wherein the at least one resistive element and the one or more reactive elements provide the high frequency impedance approximately equal to the characteristic impedance of the lead such that energy of a high frequency wave induced by exposure of the lead to a high frequency electromagnetic field at high frequencies comprising at least one of 27 MHz, 64 MHz, and 128 MHz is dissipated closer to the proximal end of the lead conductor than the distal end.

49. The device of claim 47, wherein the at least one resistive element of the passive lossy circuit provides a resistance approximately equal to the characteristic impedance of the lead.

50. The device of claim 47, wherein the housing contains electronic circuitry and the device further comprises a feedthrough for use in connecting the electronic circuitry to the lead, and further wherein the passive lossy circuit is formed at least in part by the feedthrough.

51. The device of claim 48, wherein the housing contains electronic circuitry and the device further comprises a feedthrough for use in connecting the electronic circuitry to the lead, and further wherein the passive lossy circuit is formed at least in part by the feedthrough.

* * * * *